(12) United States Patent
Guo et al.

(10) Patent No.: US 12,262,871 B1
(45) Date of Patent: Apr. 1, 2025

(54) DUAL-BEAM DUAL-MAGNET CAPSULE FOR ENDOSCOPY IN STOMACH

(71) Applicant: Hong Kong Applied Science and Technology Research Institute Company Limited, Hong Kong (HK)

(72) Inventors: Huimin Guo, Hong Kong (HK); Wenchao Wu, Hong Kong (HK); Chun Kit Lau, Hong Kong (HK)

(73) Assignee: Hong Kong Applied Science and Technology Research Institute Company Limited (HK)

( * ) Notice: Subject to any disclaimer, the term of this patent is extended or adjusted under 35 U.S.C. 154(b) by 0 days.

(21) Appl. No.: 18/659,264

(22) Filed: May 9, 2024

Related U.S. Application Data

(63) Continuation-in-part of application No. 18/581,563, filed on Feb. 20, 2024.

(51) Int. Cl.
| | |
|---|---|
| *A61B 1/04* | (2006.01) |
| *A61B 1/00* | (2006.01) |
| *A61B 1/06* | (2006.01) |

(52) U.S. Cl.
CPC .......... *A61B 1/041* (2013.01); *A61B 1/00016* (2013.01); *A61B 1/00032* (2013.01); *A61B 1/00158* (2013.01); *A61B 1/063* (2013.01); *A61B 1/0655* (2022.02); *A61B 1/0684* (2013.01)

(58) Field of Classification Search
CPC ... A61B 1/041; A61B 1/00158; A61B 1/0655; A61B 1/0684
See application file for complete search history.

(56) References Cited

U.S. PATENT DOCUMENTS

| | | | |
|---|---|---|---|
| 9,968,290 B2* | 5/2018 | Belson | A61B 1/041 |
| 2005/0004474 A1* | 1/2005 | Iddan | A61B 1/0607 |
| | | | 600/476 |
| 2005/0043583 A1 | 2/2005 | Killmann et al. | |

(Continued)

FOREIGN PATENT DOCUMENTS

| | | |
|---|---|---|
| CN | 102641124 A | 8/2012 |
| CN | 105167734 A | 12/2015 |

(Continued)

OTHER PUBLICATIONS

ISR and Written Opinion, PCT/CN2024/097746, Nov. 14, 2024.

*Primary Examiner* — John P Leubecker
*Assistant Examiner* — Jae Woo
(74) *Attorney, Agent, or Firm* — Stuart T. Auvinen; gPatent LLC

(57) ABSTRACT

A swallowable capsule has a primary magnet along a long axis that aligns between movable electromagnets in a magnetic endoscopy machine. A flip magnet is orthogonal to the long axis. The capsule is rolled around the long axis to flip orientation of a side camera on a side of the capsule. An external base electromagnet below the patient's feet is energized to roll the capsule. The base magnet acts on the flip magnet but not on the orthogonal primary magnet when the long axis is orthogonal to a magnetic axis of the base electromagnet. Most components such as a controller, the side camera, a side laser, batteries, and an antenna, are mounted to a long Printed Circuit Board (PCB) along the long axis, while a front camera and laser are mounted to a front PCB that is mounted orthogonally to a front edge of the long PCB.

5 Claims, 16 Drawing Sheets

(56) References Cited

U.S. PATENT DOCUMENTS

| | | | | |
|---|---|---|---|---|
| 2006/0004255 | A1* | 1/2006 | Iddan | A61B 1/041 600/593 |
| 2008/0300453 | A1* | 12/2008 | Aoki | A61B 1/00158 600/118 |
| 2010/0268025 | A1* | 10/2010 | Belson | A61B 1/00158 600/109 |
| 2012/0149981 | A1* | 6/2012 | Khait | A61B 1/041 600/114 |
| 2018/0084976 | A1* | 3/2018 | Duan | A61B 5/062 |
| 2018/0213207 | A1* | 7/2018 | Wilson | H04N 17/002 |
| 2019/0282075 | A1* | 9/2019 | Deng | A61B 1/00158 |
| 2019/0365210 | A1* | 12/2019 | Duan | A61B 1/041 |
| 2020/0323422 | A1* | 10/2020 | Duan | A61B 1/015 |

FOREIGN PATENT DOCUMENTS

| | | | |
|---|---|---|---|
| CN | 107158552 | A | 9/2017 |
| CN | 210784245 | U | 6/2020 |
| CN | 210871460 | U | 6/2020 |
| CN | 111568347 | A | 8/2020 |
| CN | 113768448 | A | 12/2021 |
| CN | 215191392 | U | 12/2021 |
| CN | 114287870 | A | 4/2022 |
| JP | 2009050400 | A | 3/2009 |
| JP | 5543684 | B2 | 7/2014 |
| JP | 2016140561 | A | 8/2016 |
| KR | 20130017854 | A | 2/2013 |

* cited by examiner

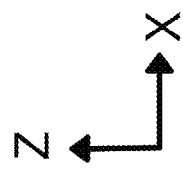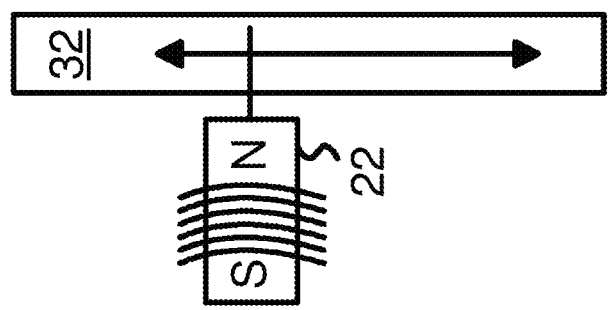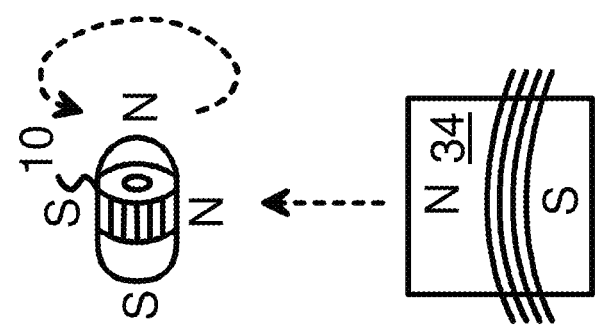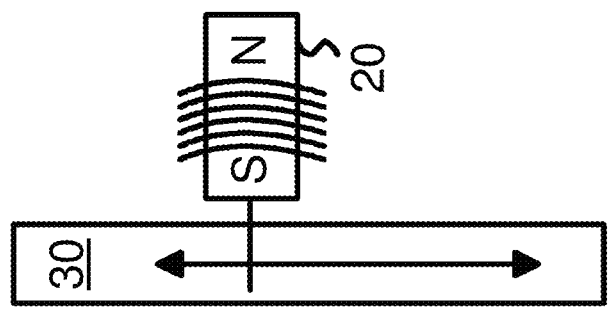
FIG. 6

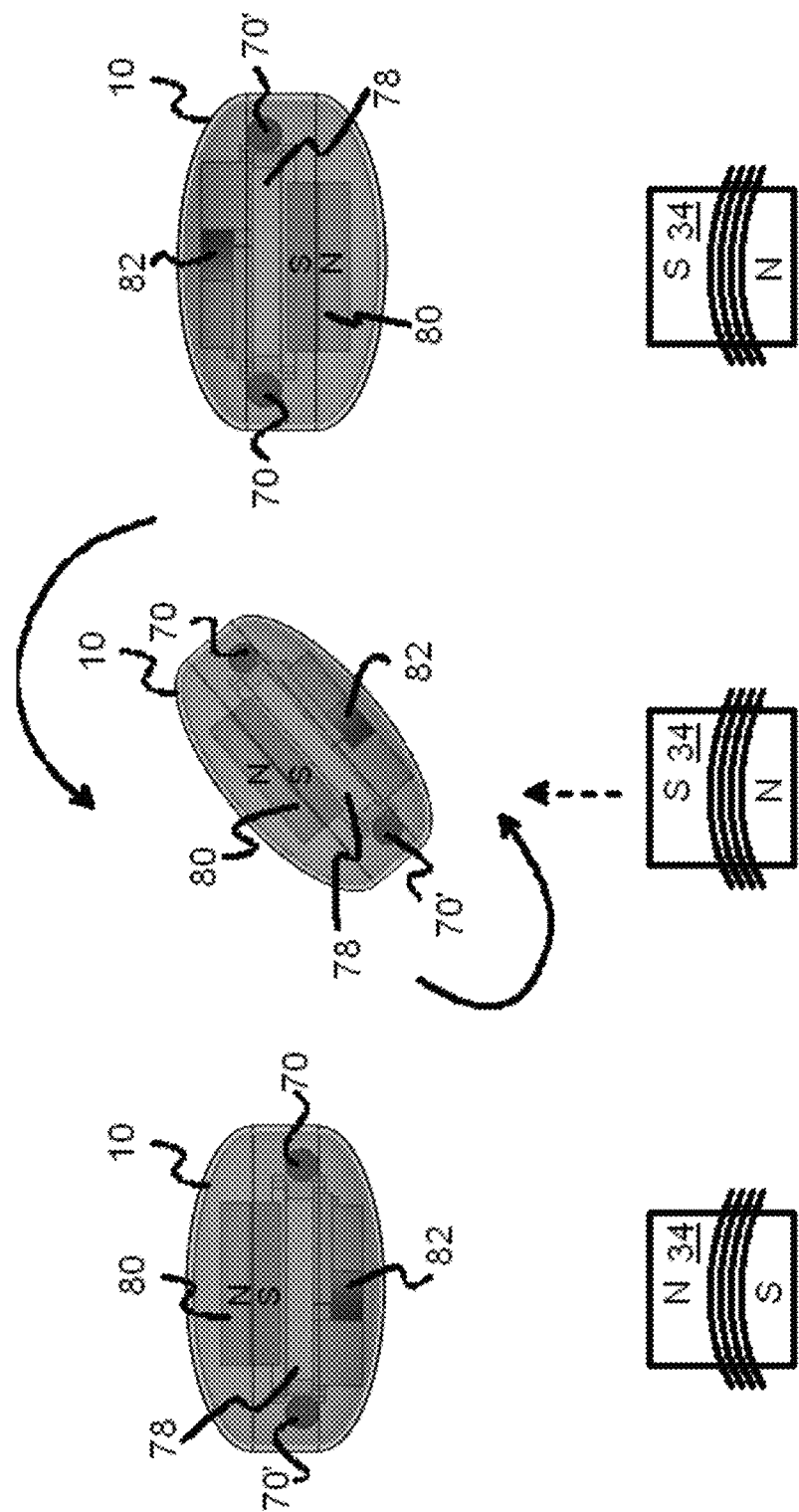

FLIP

SCAN PITCH ANGLE

RE-SCAN PITCH ANGLE

FRONT TOP VIEW

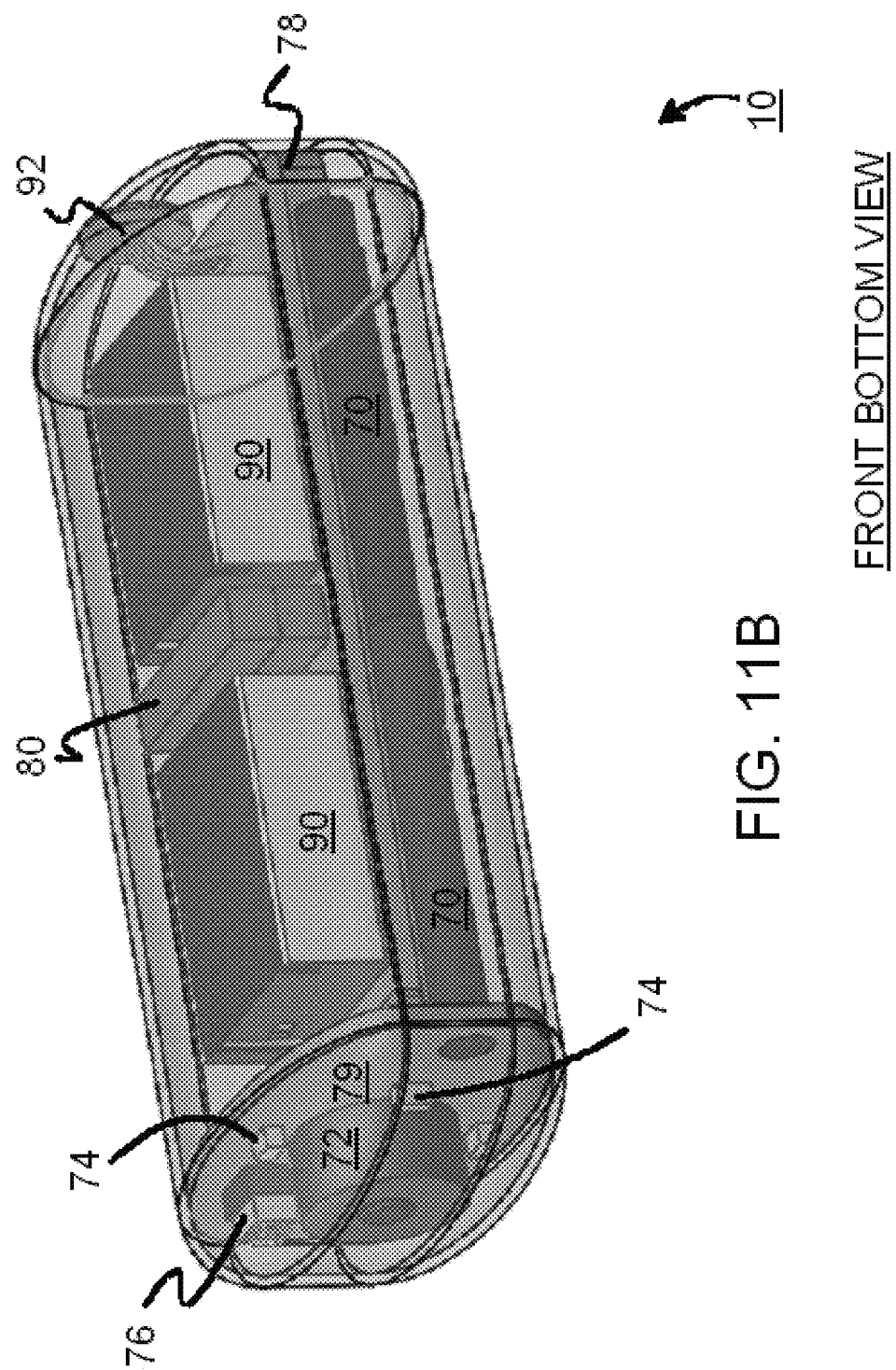
FIG. 11B    FRONT BOTTOM VIEW

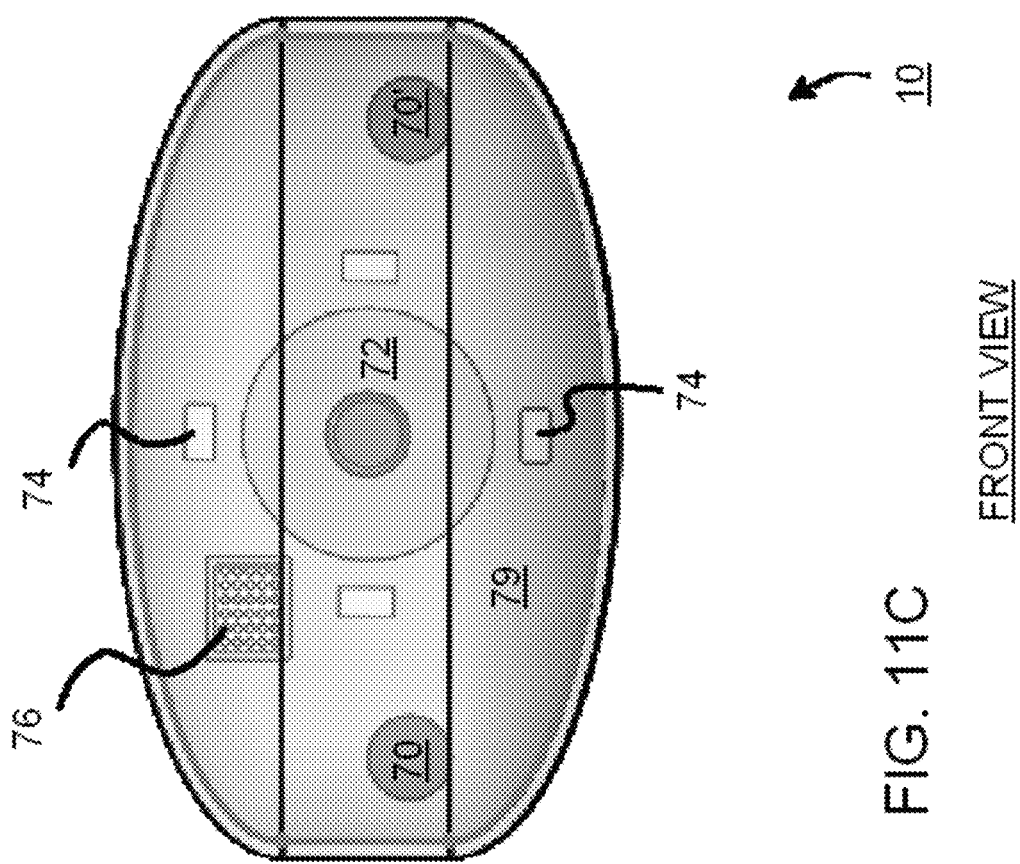
FIG. 11C  FRONT VIEW

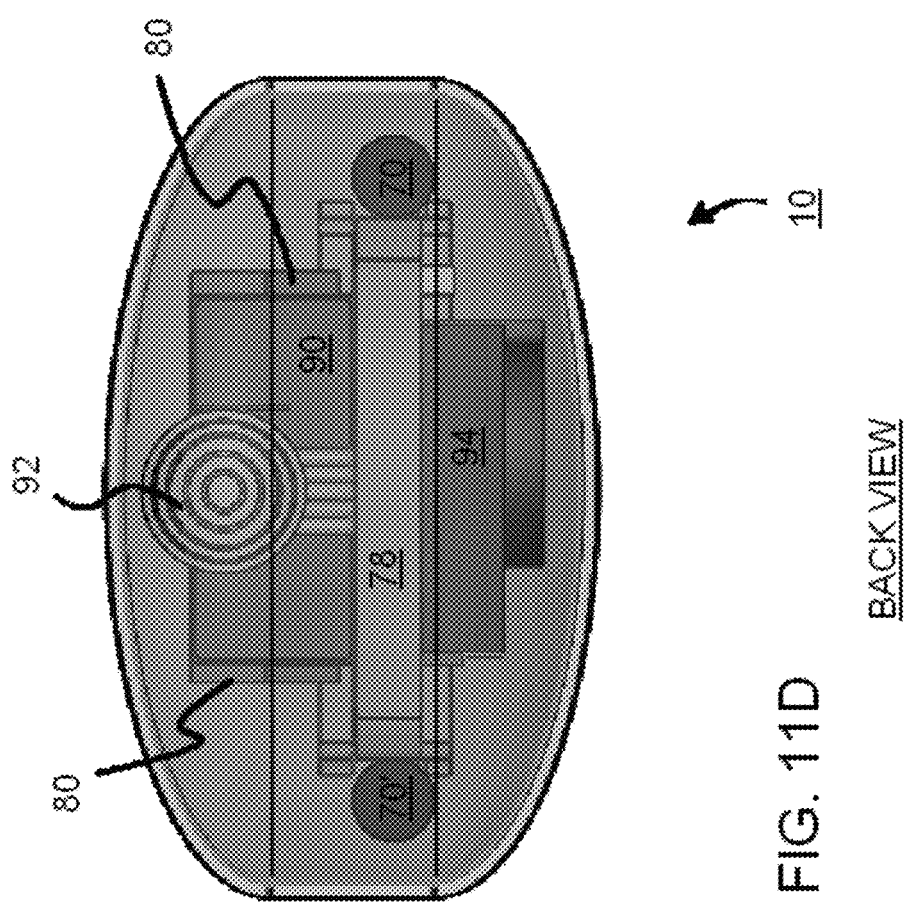
FIG. 11D  BACK VIEW

DUAL-BEAM DUAL-MAGNET CAPSULE FOR ENDOSCOPY IN STOMACH

RELATED CASE

This application is a Continuation-In-Part (CIP) of U.S. Ser. No. 18/581,563, filed Feb. 20, 2024.

FIELD OF THE INVENTION

This invention relates to medical screening devices, and more particularly to capsule endoscopy of the stomach.

BACKGROUND OF THE INVENTION

Routine medical screenings can save lives as early detection before symptom onset can allow for an earlier diagnosis and intervention before disease progression. Colonoscopies are routinely performed every 10 years for certain age groups to screen entire populations for signs of cancer long before symptoms develop. Endoscopies likewise show promise for screenings for stomach problems.

More recently, magnetic capsule endoscopy is being developed. The patient swallows a small capsule that contains a camera, light source, battery, wireless transmitter, and magnet. The patient then lies on or stands in a magnetic endoscopy machine that moves the location and angle of the capsule in the patient's stomach using movable magnets outside the stomach. Images taken by the capsule are sent wirelessly for display or analysis.

FIG. 1 shows a magnetic endoscopy capsule in a patient's stomach that is being moved by external magnets. Capsule 11 is inside the patient's stomach while electromagnets 12, 14 are external magnets that move outside the patient's body but near his stomach. When both electromagnets 12, 14 are energized by current flowing through their coils, they generate a magnetic field that exerts a magnetic force on a fixed magnet within capsule 11. While the north (N) and south(S) poles of the fixed magnet in capsule 11 are fixed, the N and S poles of electromagnets 12, 14 can be flipped by reversing the direction of current flow through the coils. In this example, electromagnet 12 has a N pole nearest capsule 11 that attracts the S pole inside capsule 11, while electromagnet 14 has a S pole facing capsule 11, attracting the N pole inside capsule 11.

Electromagnets 12, 14 can be physically moved, such as by being attached to a track mechanism. When both electromagnets 12, 14 are energized and moved upward, then capsule 11 is pulled upward. When both electromagnets 12, 14 are energized and moved downward, capsule 11 is pulled downward, even when within the patient's stomach.

FIG. 2 shows pitching the capsule upward. When electromagnet 12 is energized and moved downward, while electromagnet 14 is energized and moved upward, the S pole of the magnet inside capsule 11 is pulled downward while the N pole inside capsule 11 is pulled upward. Thus capsule 11 is angled or pitched upward. When the camera in capsule 11 is on the right end of capsule 11, near the N pole, the camera is pitched up, allowing the camera to capture images of the upper portion of the stomach. The top of the stomach is facing up and the bottom of the stomach is facing down in this drawing example.

The pitch angle is limited due to the locations of electromagnets 12, 14 and distance to the stomach. The track or other mechanism to move electromagnets 12, 14 may have a limited size, which also limits the pitch angle. It is difficult to achieve a large pitch angle and point the camera at the end of capsule 11 up toward the top of the stomach. Endoscopy machine layout and its geometry thus may limit the pitch angle to 45 degrees as an example. Imaging the top and bottom of the stomach may be difficult when capsule 11 only has a single camera at its tip end.

To solve the problem of imaging the top and bottom of the stomach when capsule 11 has a limited pitch, a second camera can be added. The second camera can be added on the side of capsule 11 and face outward from the side rather than the end where the tip-end camera is located. This side camera can then image the top of the stomach when the pitch is zero (FIG. 1).

FIG. 3 highlights a roll problem with endoscopy capsules. The fixed magnet within capsule 11 is often placed along or parallel to the longer axis, such as longitudinal axis 16. Since longitudinal axis 16 is along the magnetic axis, capsule 11 tends to align itself to this axis when electromagnets 12, 14 are positioned along this axis, such as in FIGS. 1, 2. However, capsule 11 itself may roll around longitudinal axis 16 since electromagnets 12, 14 exert a force along or parallel to longitudinal axis 16.

This uncontrolled rolling of capsule 11 along longitudinal axis 16 is undesirable in some situations, such as when a second camera is added on the side of capsule 11. This side camera could be facing in any of the 360 degrees around longitudinal axis 16 since the rotational angle is not controlled but is random and varying.

FIG. 4 shows a prior art magnetic endoscopy capsule. Capsule 11 has fixed magnet 23 that is oriented parallel to the longitudinal axis. Camera 17 is placed near the right end which is near the N pole. Multiple circuit boards 15 can each be a small Printed Circuit Board (PCB) having a circular shape to fit inside capsule 11. Flexible cabling 13 can connect boards 15. Other components 19 such as Integrated Circuits (ICs) can be mounted to boards 15. Cutouts or holes in boards 15 can be sized to fit magnet 23 during assembly.

The multiple boards 15 and cabling 13 can increase cost and complexity and can require that capsule 11 be increased in size. Rather than have multiple boards 15 and cabling 13, a single larger board is desired.

What is desired is a magnetic endoscopy capsule. An endoscopy capsule that allows for control of the roll around the longitudinal axis is desired. A capsule that allows for imaging of the top and bottom of the stomach when the pitch angle is limited is also desired. An endoscopy capsule having most components mounted to a single interior board is desirable to reduce or eliminate cabling.

BRIEF DESCRIPTION OF THE DRAWINGS

FIG. 6 highlights flipping the capsule using the base magnet under the person's feet.

FIGS. 8A-8C show cross-sectional views of rolling of the capsule using the flip magnet.

FIGS. 11A-11D show the magnetic endoscopy capsule in more detail.

DETAILED DESCRIPTION

The present invention relates to an improvement in magnetic endoscopy capsules. The following description is presented to enable one of ordinary skill in the art to make and use the invention as provided in the context of a particular application and its requirements. Various modifications to the preferred embodiment will be apparent to those with skill in the art, and the general principles defined herein may be applied to other embodiments. Therefore, the present invention is not intended to be limited to the particular embodiments shown and described but is to be accorded the widest scope consistent with the principles and novel features herein disclosed.

The parent application describes a magnetic endoscopy machine that has computer control of the external magnets. An automated routine energizes and moves the external magnets to position the magnetic capsule within the stomach. The patient is standing in the endoscopy machine rather than lying flat.

Figure 5:
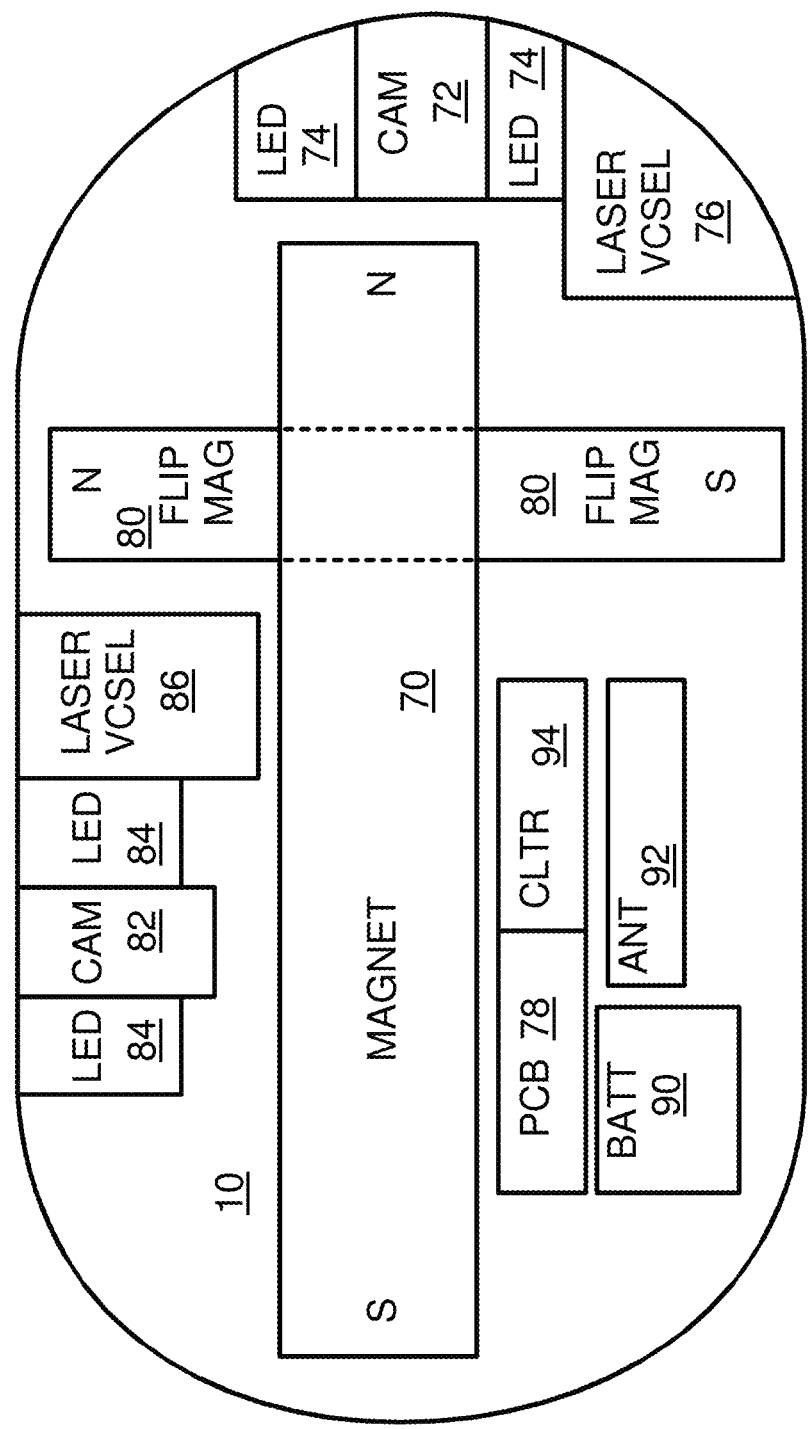
FIG. 5 is a diagram of a magnetic endoscopy capsule.

FIG. 5 is a diagram of a magnetic endoscopy capsule. Capsule 10 is relatively small and is swallowed by the person just before endoscopy screening. Capsule 10 can first be activated or woken up before being handed to the person so that battery 90 does not get depleted before the screening starts.

Capsule 10 executes programs on controller 94 that is mounted to Printed Circuit Board (PCB) 78 that connects power from battery 90 to controller 94 and to other components on or off PCB 78 such as cameras 72, 82 and their Light Emitting Diodes (LED) 74, 84, and lasers 76, 86.

Lasers 76, 86 each can be a Vertical-Cavity Surface-Emitting Laser (VCSEL) that have an emitter that generates a laser beam with a fixed angle that is reflected off the inner walls of the stomach. The returned laser beam is then received by an image sensor, such as a CCD or CMOS sensor. The received laser beam is then analyzed to measure the distance between the capsule and the inner stomach wall. The physical shape of the stomach can then be mapped out by lasers 76, 86 before image capture by cameras 72, 82. An Inertial Measurement Unit (IMU) inside capsule 10 can provide the position of capsule 10 during mapping. The IMU can be part of controller 94 or can be a separate component mounted to PCB 78.

The tip or end of capsule 10 is provided with laser 76, camera 72, and its LED's 74, to permit laser distance-measurement and image capture from the front end of capsule 10. The longer side of capsule 10 is also fitted with laser 86, camera 82, and its LEDs 84 to permit laser distance-measurement and image capture from the side of capsule 10. LEDs 74 provide front-facing illumination for images captured by front camera 72, while LEDs 84 provide side-facing illumination for images captured by side camera 82.

Cameras 72, 82 and lasers 76, 86 are oriented within the stomach by external electromagnets 20, 22 that move capsule 10 using a magnetic force applied to primary magnet 70. During endoscopy screening, actuators and a rotating ring move within the endoscopy machine. This movement changes the magnetic field orientation and thus changes the orientation of capsule 10 to capture different images within the stomach. A sequence of such movements may be programmed into an automatic screening routine so that images of the entire stomach can be quickly captured.

Primary magnet 70 and flip magnet 80 are permanent magnets that are mounted at right angles to each other. Primary magnet 70 is larger and has a higher magnetic strength than flip magnet 80. When external electromagnets 20, 22 (FIGS. 6-7A) are energized, they exert a greater force on primary magnet 70 than on flip magnet 80 so that capsule 10 moves to align primary magnet 70 with the external magnetic field generated by electromagnets 20, 22.

During screening, after images from the upper half of the stomach are captured by side camera 82 facing upward, capsule 10 can be flipped over to cause side camera 82 to face downward so that the lower half of the stomach can be imaged by side camera 82. Base electromagnet 34 (FIGS. 6-8C) is activated when capsule 10 is in or near the X-Y plane. Base electromagnet 34 is then nearly parallel to primary magnet 70 so that only small net force is applied to primary magnet 70 from base electromagnet 34. Thus base electromagnet 34 exerts a magnetic force mostly on flip magnet 80, not as much on primary magnet 70. This force on flip magnet 80 causes capsule 10 to rotate along the longitudinal axis parallel to primary magnet 70, flipping camera 82 to face downward rather than upward.

Images captured by cameras 72, 82 are sent to controller 94 or its memory (not shown) and are then wirelessly transmitted by antenna 92 to a wireless transceiver on the automated magnetic endoscopy machine. The received images can then be stored and analyzed by an automated screening program. When abnormalities are detected, such as dark colored spots on the stomach wall, then the program can instruct the actuators and rotating ring to move external magnets to orient capsule 10 to point a camera at the location of the abnormality so that further images may be captured. The program may also move capsule 10 closer to the abnormality such as by increasing power to electromagnet 20 or to electromagnet 22 until capsule 10 is in the desired location for close-up image capture.

FIG. 6 highlights flipping the capsule using the base magnet under the person's feet. During endoscopy screening, after images from the upper half of the stomach are captured by side camera 82 facing upward, capsule 10 can be flipped over to cause side camera 82 to face downward so that the lower half of the stomach can be imaged by side camera 82.

Capsule 10 is inside the patient's stomach while external electromagnets 20, 22 are external to and beside the stomach. Base electromagnet 34 is below the patient's feet. Base electromagnet 34 does not move, but external electromagnets 20, 22 are moved up and down in the Z direction by actuators 30, 32. Actuators 30, 32 can include a track mechanism to move external electromagnets 20, 22 up and down along the track. Actuators 30, 32 can be mounted to a rotating ring, allowing external electromagnets 20, 22 to rotate around the patient's body. Thus external electromagnets 20, 22 can be placed at any angle around a vertical axis through the patent's head, stomach, and standing body.

Base electromagnet 34 under the patient's feet is activated when capsule 10 is close to the X-Y plane and is not pitched up or down by a large amount. Actuators 30, 32 may be placed in the same or nearly same Z location or setting so that electromagnet 20 and electromagnet 22 are in the same X-Y plane parallel to the floor the patient stands on. Alternatively, external electromagnets 20, 22 may have different Z values so that capsule 10 is pitched only slightly.

Base electromagnet 34 is then nearly parallel to primary magnet 70 so that only a small net force is applied to primary magnet 70 from base electromagnet 34. Thus base electromagnet 34 exerts a magnetic force mostly on flip magnet 80, not as much on primary magnet 70.

When the automated program energizes base electromagnet 34, the force exerted by base electromagnet 34 onto flip magnet 80 causes capsule 10 to rotate along the longitudinal axis parallel to primary magnet 70, flipping side camera 82 to face downward rather than upward.

The flip force required is relatively small since the rotational motion of capsule 10 does not face as much resistance in the stomach as does translational motion of capsule 10. Thus base electromagnet 34 does not have to be powerful, although the greater distance to capsule 10 (below feet to stomach) may require more magnetic force than the closer electromagnets 20, 22.

Base electromagnet 34 may be placed below a stationary disk under the patient's feet. Base electromagnet 34 is normally de-energized and turned off but can be turned on briefly to flip capsule 10. Base electromagnet 34 exerts a downward magnetic field in the vertical or Z direction.

Figure 7A:
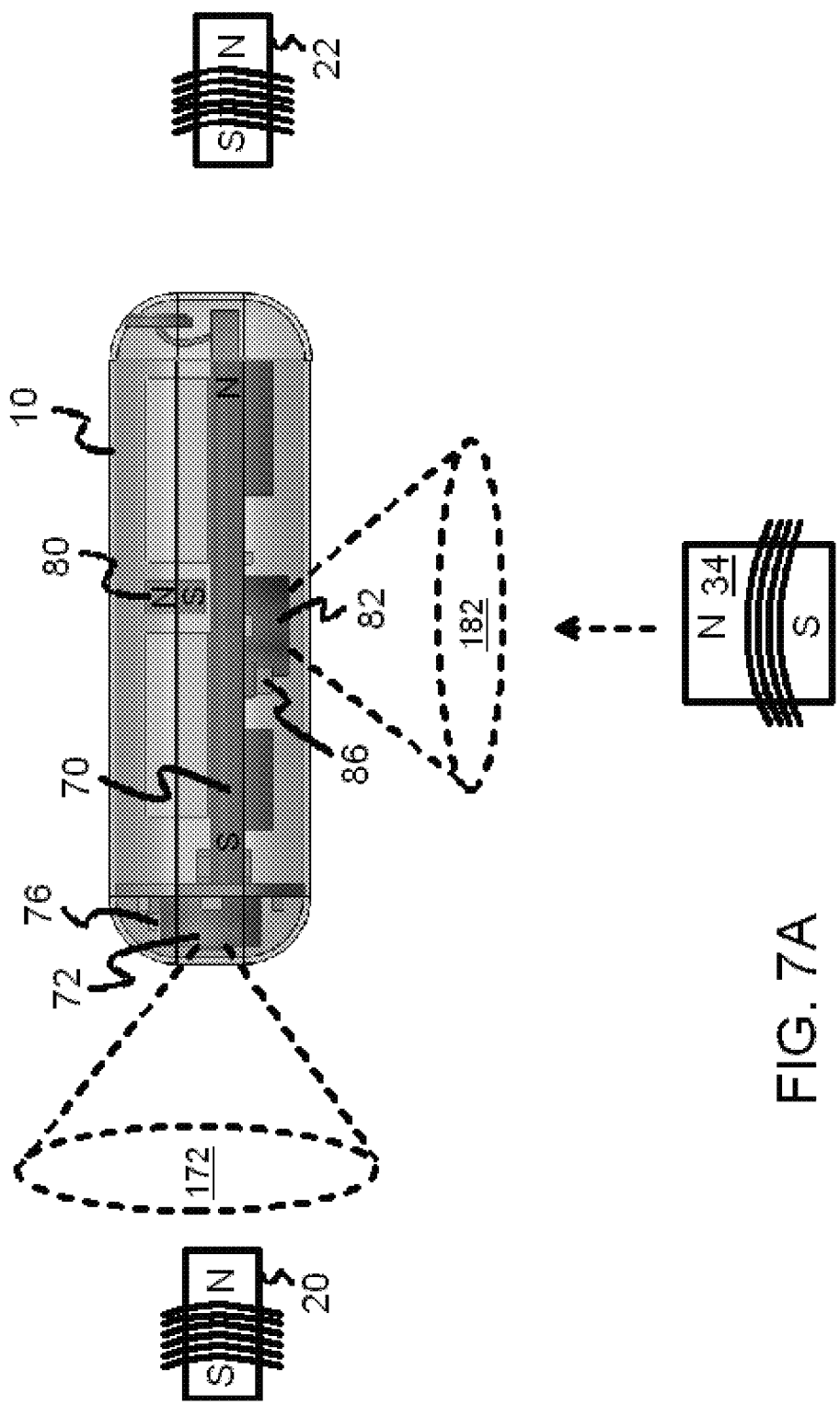
FIGS. 7A-7C show flipping of the capsule.
Figure 7B:
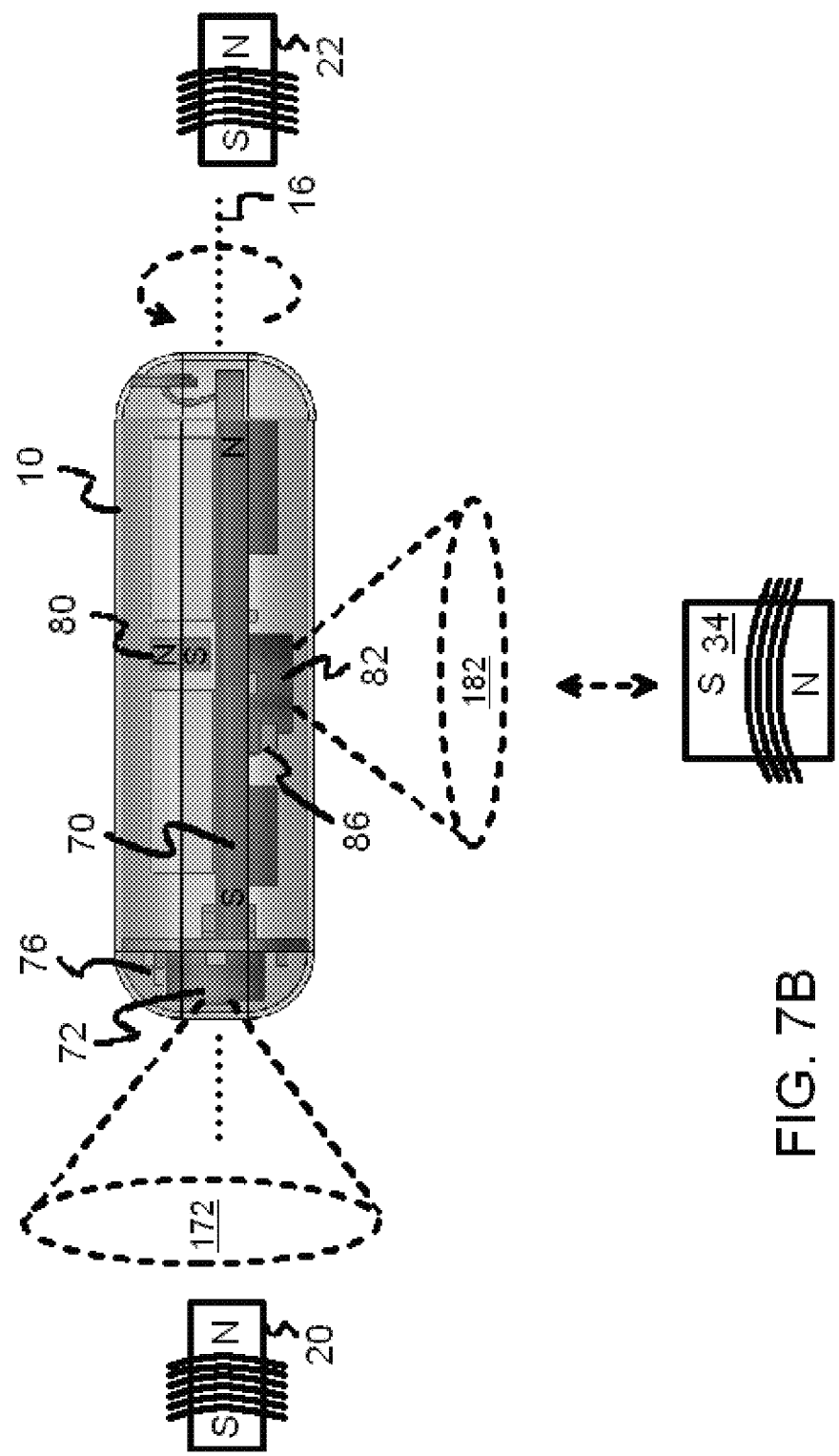
Figure 7C:
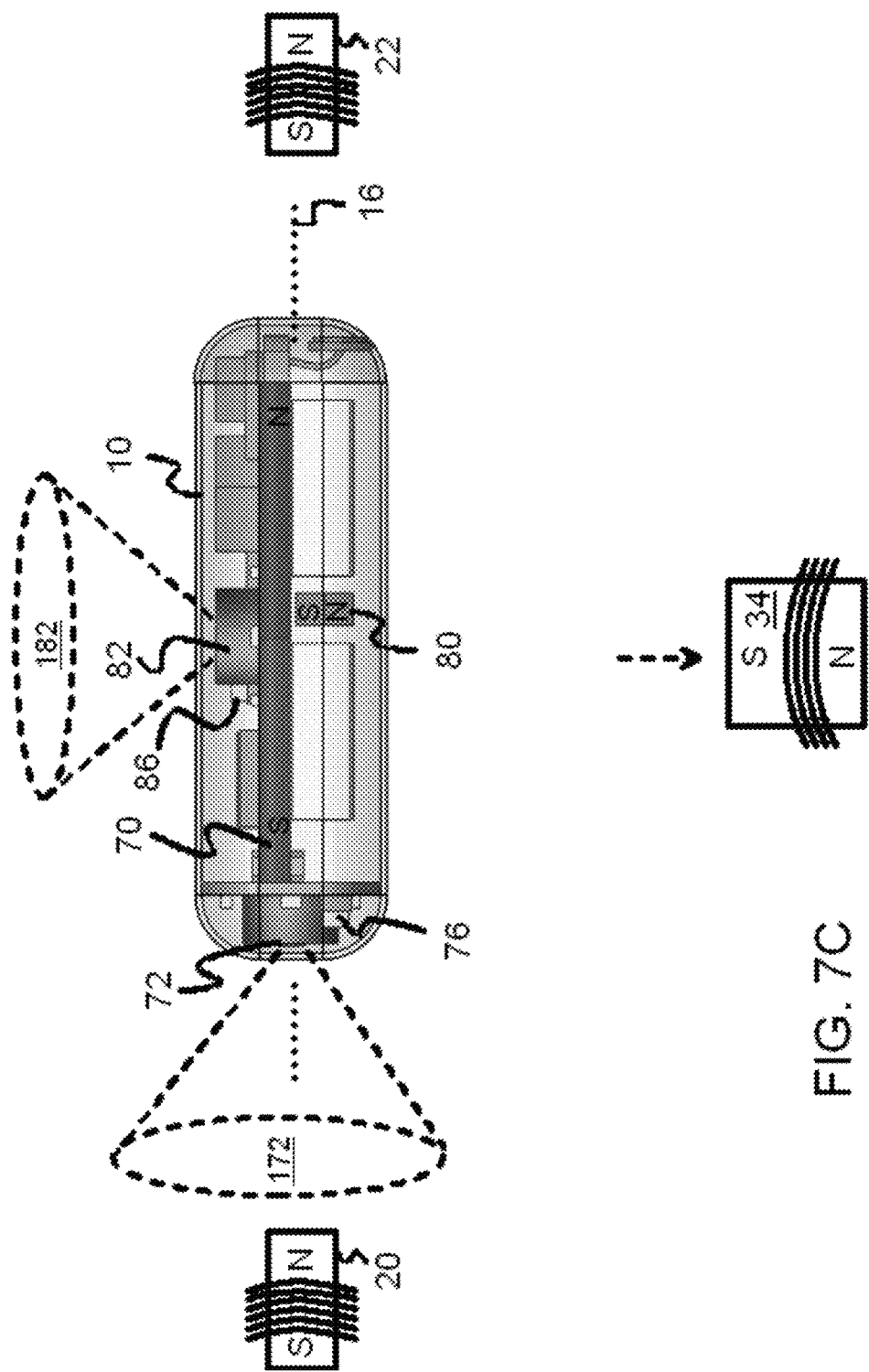

FIGS. 7A-7C show flipping of the capsule. In FIG. 7A, capsule 10 has primary magnet 70 along a longitudinal axis. External electromagnets 20, 22 when energized exert a magnetic force on primary magnet 70 that forces capsule 10 to align to a line between external electromagnets 20, 22. The magnetic force generated by external electromagnets 20, 22 is sufficient to overcome any resistance to movement of capsule 10 by the viscosity of various stomach fluids.

After a delay for any movement of capsule 10, capsule 10 becomes aligned to external electromagnets 20, 22 and stops moving. Front camera 72 faces left and can capture images within front cone 172. Likewise front laser 76 points into the center of front cone 172 so that laser light is reflected back into the image sensor for front camera 72, or to a nearby separate image sensor for laser light.

Side camera 82 faces downward and can capture images within side cone 182. Likewise side laser 86 points into the center of side cone 182 so that laser light is reflected back into the image sensor for side camera 82, or to a nearby separate image sensor for laser light.

The polar axis of primary magnet 70 includes its N and S poles, and is concurrent with or parallel to the longitudinal axis of capsule 10. Primary magnet 70 aligns to a line between external electromagnets 20, 22 when they are energized, causing capsule 10 to move as needed. This polar axis of primary magnet 70 is horizontal in FIGS. 7A-7C.

Flip magnet 80 has a polar axis, that passes through its N and S poles, that is vertical. Since flip magnet 80 is much smaller than primary magnet 70, the force applied by external electromagnets 20, 22 onto primary magnet 70 is much greater than the force applied to flip magnet 80 for most pitches of capsule 10. If capsule 10 were vertical, with flip magnet 80 aligned horizontally between external electromagnets 20, 22, then flip magnet 80 might have a greater translational force than primary magnet 70 which would be vertically aligned, however the magnetic torque from primary magnet 70 would still be greater than the torque from flip magnet 80. Also any movements of the stomach fluid would push capsule 10 out of this quasi-equilibrium state and allow the larger primary magnet 70 to align.

Thus capsule 10 tends to align primary magnet 70 to external electromagnets 20, 22 despite any opposing force from flip magnet 80. When capsule 10 is aligned horizontally, flip magnet 80 exerts little or no force due to external electromagnets 20, 22 which have a magnetic field that is 90 degrees out of alignment to that of flip magnet 80. Flip magnet 80 has a magnetic pole that is orthogonal to the magnetic pole of primary magnet 70 and between external electromagnets 20, 22. Having magnetic poles that are orthogonal or orthogonal to each other allows primary magnet 70 and flip magnet 80 to respond to different external magnets without interfering with each other.

Base electromagnet 34 is placed below the patient's feet, and has a magnetic pole that is vertical. External electromagnets 20, 22 are placed to the sides of the patient's stomach, and have magnetic poles that are horizontal. When base electromagnet 34 is energized with a current direction that causes its N pole to be up and its S pole to be down, the S pole of flip magnet 80 is drawn downward toward base electromagnet 34, and its N pole is repulsed by base electromagnet 34. The stronger magnetic field generated by external electromagnets 20, 22 can prevent capsule 10 from moving downward toward base electromagnet 34, or base electromagnet 34 can be pulsed on for a very short period of time to minimize any downward (−Z) movement.

In FIG. 7B, the current direction of base electromagnet 34 has been reversed. Now the S pole of base electromagnet 34 faces upward toward capsule 10, which has the S pole of flip magnet 80 facing downward. This is a higher-energy state and is unstable. The repulsion between the S pole of base electromagnet 34 and the S pole of flip magnet 80 causes capsule 10 to begin rotating around its longitudinal axis. Capsule 10 is small and its rotational inertia can be less that its transformational inertia so that it rotates rather than move upward away from base electromagnet 34. It may move upward slightly while also rotating. External electromagnets 20, 22 can remain energized to prevent this upward movement when base electromagnet 34 is activated.

In FIG. 7C, capsule 10 has rotated by 180 degrees around its longitudinal (horizontal) axis. Base electromagnet 34 can be turned off. Capsule 10 has been flipped or rolled by the force of base electromagnet 34 acting upon flip magnet 80. Now flip magnet 80 has its N pole facing down toward the S pole of base electromagnet 34. This is a lower energy state than that of FIG. 7B.

Front camera 72 still faces left and can capture images within front cone 172. Likewise front laser 76 points into the center of front cone 172 so that laser light is reflected back into the image sensor for front camera 72, or to a nearby separate image sensor for laser light.

Side camera 82 now faces upward and can capture images within side cone 182. Likewise side laser 86 points into the center of side cone 182 so that laser light is reflected back into the image sensor for side camera 82, or to a nearby separate image sensor for laser light. The upper wall of the stomach can now be imaged using side camera 82, or the upper stomach wall can be mapped by side laser 86.

FIGS. 8A-8C show cross-sectional views of rolling of the capsule using the flip magnet. In FIG. 8A, flip magnet 80 has a vertical polar axis with N facing up and S facing down.

There are two primary magnets that are parallel to each other in this embodiment. Primary magnet 70, 70' are placed on either side of PCB 78, which runs the length of capsule 10, orthogonal to the plane of the drawing. Thus the magnetic polar axis of primary magnet 70 is orthogonal to the plane of the drawing of FIGS. 8A-8C. Side camera 82 and side laser 86 face downward. Base electromagnet 34 has its N pole facing upward toward the S pole of flip magnet 80.

In FIG. 8B, the current direction has been reversed in base electromagnet 34 and base electromagnet 34 has been energized. The S pole of base electromagnet 34 now faces upward, repulsing the S pole of flip magnet 80 that initially faces downward, while attracting the N pole of flip magnet 80 which faces upward. This is an unstable state. So capsule 10 begins to roll about its long axis (orthogonal to the plane of the drawing). Base electromagnet 34 exerts equal forces to all parts of primary magnet 70, but exerts a greater attractive force on the N pole of flip magnet 80 than on the S pole of flip magnet 80. This unbalanced force causes flip magnet 80 and capsule 10 to rotate or roll. As rolling progresses, base electromagnet 34 continues to attract the N pole and repulse the S pole of flip magnet 80.

In FIG. 8C, flipping has finished. Now capsule 10 is in a flipped state, with the N pole of flip magnet 80 facing downward toward the S pole of base electromagnet 34. Side laser 86 and side camera 82 now both face upward. The side camera orientation has been flipped. Base electromagnet 34 can remain on to prevent stomach fluid turbulence from randomly rolling.

Figure 9:
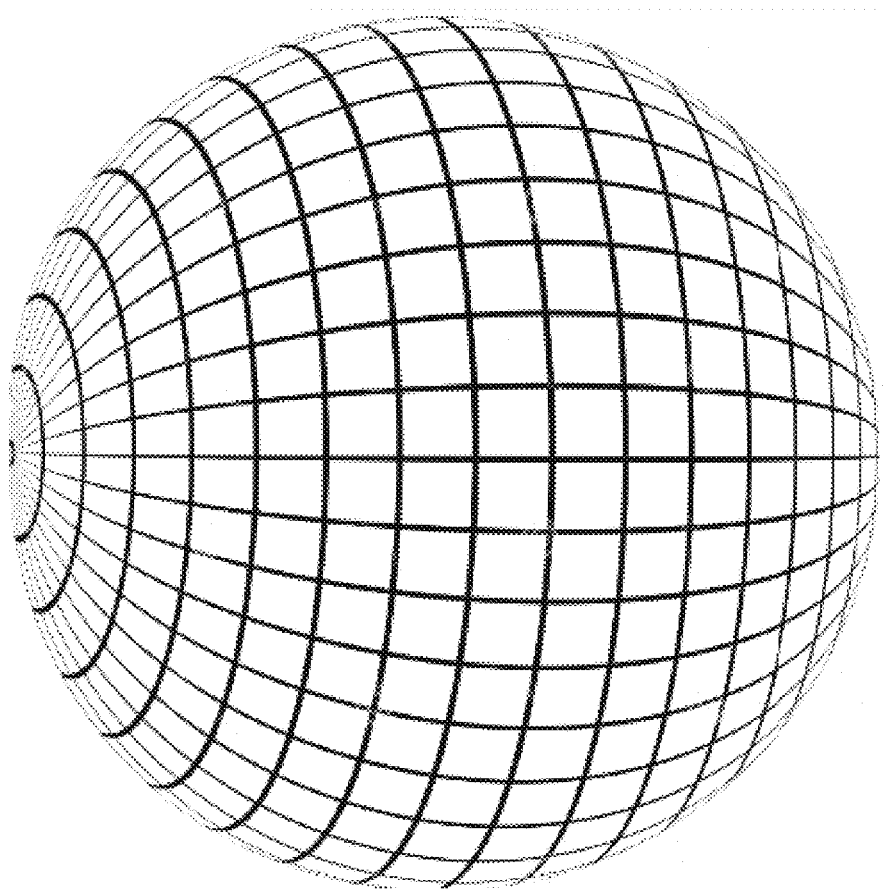
FIG. 9 is a polar coordinate map.

FIG. 9 is a polar coordinate map. VCSEL lasers 76, 86 can measure a distance that a laser beam travels from the laser source and back to the detector after reflecting off an object such as the stomach wall. For example, the laser can be pulsed on, and the time delay until the laser light is detected by the sensor can be used to determine the distance that the laser beam traveled. Alternately, the image sensor can detect a diffraction pattern. The laser beam from the laser emitter can pass through a mask that causes diffraction of the laser beam exiting the capsule. The diffracted laser beam reflects off the stomach wall and back to an image sensor on the capsule. Different distances will result in different diffraction patterns captured by the image sensor. The diffraction pattern can be analyzed to estimate the distance.

Capsule 10 can be sequenced through a series of different pitches, such as shown in FIGS. 10A-10F, and then the magnets can be rotated, such as by rotating the rotating ring, and another scan of pitches performed. Thus one longitude line is scanned and then a next longitude line is scanned until all 360 degrees have been scanned. For example, each rotation could be 10 degrees and 36 pitch scans are taken.

Capsule 10 may be moved to a different location within the stomach, such as to different Z values by using actuators 30, 32. Radial location (X,Y) can be adjusted by increasing the current to electromagnet 20 while decreasing the current to electromagnet 22, or vice-versa.

Different rotational angles and pitches of capsule 10 can allow for mapping the entire polar coordinate space for each physical location of capsule 10.

Actuators 30, 32 can be activated to increase the Z value of capsule 10, and the 360 degree distance-measurement sequence repeated for each new location of capsule 10. Also, the current through electromagnets 20, 22 can be set to uneven values to allow for capsule movement in the X direction if desired.

A polar coordinate map with measured distances to the stomach wall can be obtained for each of several physical locations of capsule 10 by pitching capsule 10 up and down by different angles, and by rotating the rotating ring and magnets through 360 degrees. These polar maps can be merged to obtain an overall map of the stomach wall.

Also, both lasers 76, 86 can be used for each measurement, obtaining two range distances for two different points on the polar coordinate map. Since lasers 76, 86 are positioned at right angles to each other within capsule 10, the polar coordinate map may be obtained more quickly and more accurately than if only one laser is used.

Figure 10C:
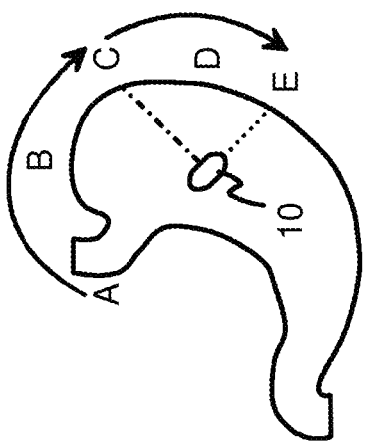
FIGS. 10A-10H show mapping the stomach wall using laser rangefinders in the capsule that is being scanned in pitch and rotated and moved.
Figure 10F:
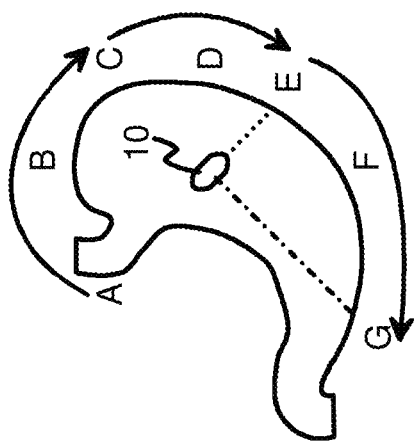
Figure 10B:
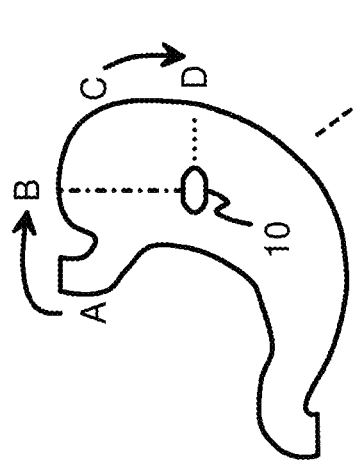
Figure 10E:
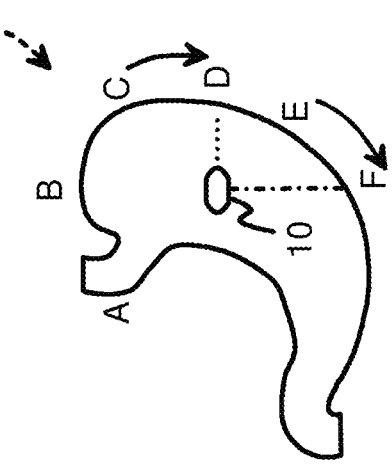
Figure 10A:
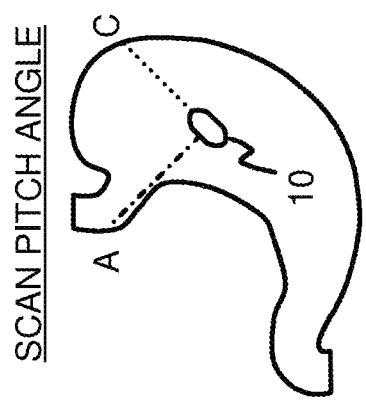
Figure 10D:
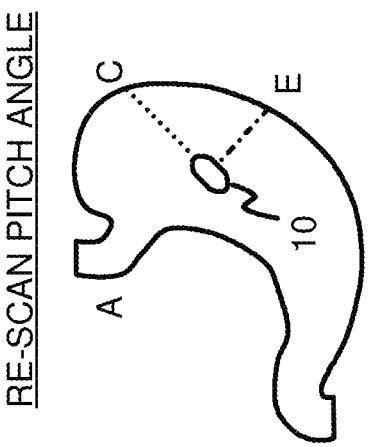

FIGS. 10A-10H show mapping the stomach wall using laser rangefinders in the capsule that is being scanned in pitch and rotated and moved. In FIG. 10A, capsule 10 has been pitched up so that front laser 76 and front LED 74 shine light on point C on the stomach wall. This light is reflected by the stomach wall and returns to the image sensor of front camera 72 where it is detected as laser or visible light. The laser light can pass through a diffraction mask in the capsule and then be reflected off the stomach wall.

The image sensor in the capsule captures the diffraction pattern. The image sensor can send this diffraction pattern to the controller for analysis to determine the distance from the capsule to the stomach wall. This diffraction pattern changes with distance. Alternately, a time delay of the laser light emission to detection can be used to determine the distance from capsule 10 to the stomach wall at point C. This distance can be added to the spherical map of the stomach (FIG. 9) for point C.

Also in FIG. 10A, capsule 10 is pitched up so that side laser 86 and side LED 84 shine light on point A on the stomach wall. This light is reflected by the stomach wall and returns to the image sensor of side camera 82 where it is detected as laser or visible light. The diffraction pattern or the time delay of the laser light emission to detection can be used to determine the distance from capsule 10 to the stomach wall at point A, and this distance can be added to the spherical map of the stomach (FIG. 9) for point A.

In FIG. 10B, capsule 10 has been pitched flat so that front laser 76 and front LED 74 shine light on point D on the stomach wall. This light is reflected by the stomach wall and returns to the image sensor of front camera 72 where it is detected as laser or visible light. The diffraction pattern or the time delay of the laser light emission to detection can be used to determine the distance from capsule 10 to the stomach wall at point D. This distance can be added to the spherical map of the stomach (FIG. 9) for point D.

Also in FIG. 10B, side laser 86 and side LED 84 shine light on point B on the stomach wall. This light is reflected by the stomach wall and returns to the image sensor of side camera 82 where it is detected as laser or visible light. The diffraction pattern or the time delay of the laser light emission to detection can be used to determine the distance from capsule 10 to the stomach wall at point B, and this distance can be added to the spherical map of the stomach (FIG. 9) for point B.

In FIG. 10C, capsule 10 is pitched down so that side laser 86 bounces light off point C while front laser 76 bounces laser light off point E. While laser range-finding to 5 discrete points A-E have been shown in FIGS. 10A-10C, there may be many smaller pitch changes between FIGS. 10A and 10C, so that distances to more than 5 points have been obtained. Thus the stomach wall between points A and E can be mapped for a particular rotational angle (longitudinal line of FIG. 9). Note that these points A-E cover only half of a full circle and do not include points in the lower part of the stomach.

In the middle of the pitch scan, when the pitch is zero, such as in FIG. 10B, a control program can energize base electromagnet 34 to flip capsule 10 (FIG. 6) so that side laser 86 and side camera 82 face down (FIG. 10E) instead of up (FIG. 10B). Then capsule 10 can be pitched up (FIG. 10D) so that front laser 76 shines on point C and side laser 86 shines on point E, allowing distances to points C and E to be obtained. In FIG. 10E capsule 10 is pitched flat so that front laser 76 shines on point D and side laser 86 shines on point F, allowing distances to points D and F to be obtained. In FIG. 10F capsule 10 is pitched down so that front laser 76 shines on point E and side laser 86 shines on point G, allowing distances to points E and G to be obtained.

Thus the ranges to points A to G are obtained in a single pitch scan for a particular rotation angle. When intermediate pitches are inserted between those of FIG. 10A-10F, many points can be ranged between A and G for a more detailed map of the stomach wall. Note that one quadrant of the stomach wall, between points G and A, is not mapped in the single pitch scan.

Figure 10H:
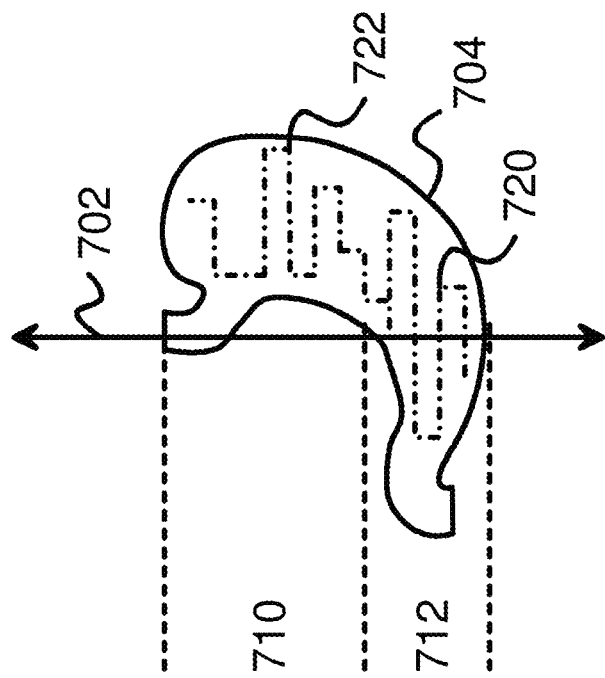
Figure 10G:
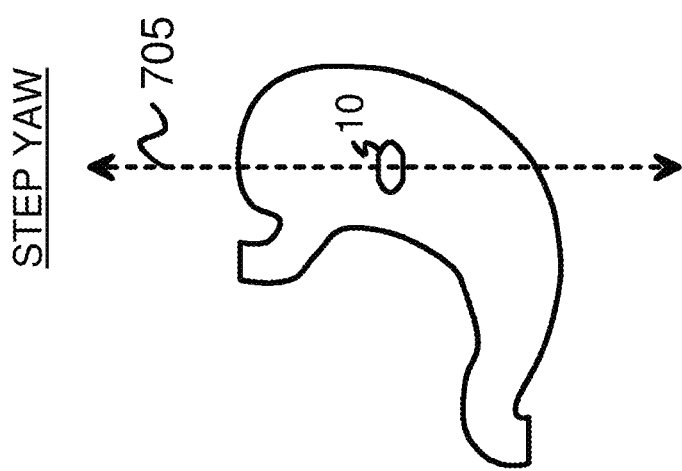

In FIG. 10G, the rotational angle or yaw is changed. Capsule 10 is rotated by the control program rotating external electromagnets 20, 22 around centerline 705, which is approximately the standing patient's centerline that also passes through the stomach. After the yaw angle is changed, then the pitch scan of FIGS. 10A-10F can be repeated for that yaw angle. The yaw angle can be changed again and another pitch scan taken. Each yaw angle can generate distance data for one longitudinal line (FIG. 9). When the yaw angle is stepped through a full circle (360 degrees or 2*pi) then the distances for the missing quadrant of points G to A are also covered as the opposite hemisphere is scanned.

Figure 1:
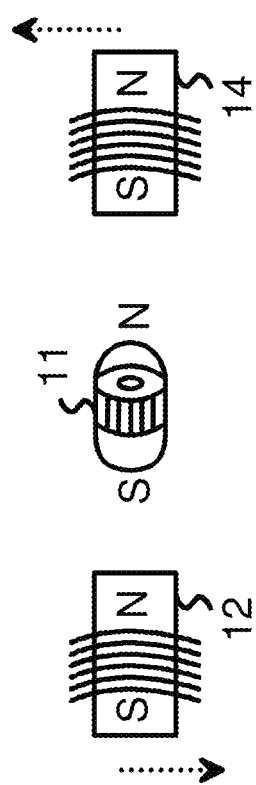
FIG. 1 shows a magnetic endoscopy capsule in a patient's stomach that is being moved by external magnets.
Figure 2:
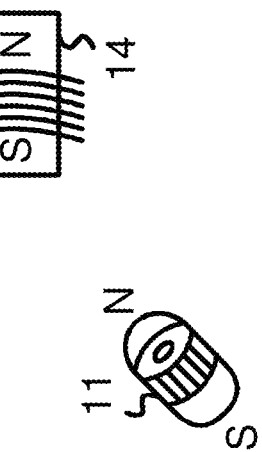
FIG. 2 shows pitching the capsule upward.
Figure 3:
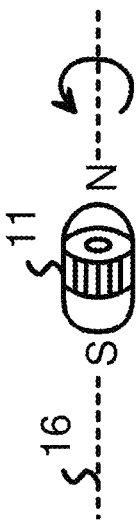
FIG. 3 highlights a roll problem with endoscopy capsules.

The control program sequences the range of pitch changes (FIGS. 10A-10F) using actuators 30, 32 to pitch external electromagnets 20, 22 (FIG. 2) and then rotates external electromagnets 20, 22 around centerline 705 of the patient (FIG. 10G), then repeating the pitch scan of FIGS. 10A-10F.

The process can be repeated for each rotational angle to capture distance data for each longitudinal line (FIG. 9) until the full spherical map has been generated. Finally, capsule 10 may be moved to a different X, Y, Z position and a new spherical map generated by repeating the process. FIG. 10H shows path 720 of physical locations of capsule 10, and a spherical map may be taken for any points along path 720.

In FIG. 10H, once capsule 10 enters the stomach, the lasers measure distances to the stomach walls as the capsule moves within the stomach. The control program generates stomach map 704 which is a 3D map of the stomach calculated from the laser distance-measurement data and inertial data from the capsule on it's location or movements. The control program can activate electromagnets 20, 22, actuators 30, 32, and a rotational motor to adjust the position of capsule 10 within the stomach, or within an expected position of the stomach when the stomach map is incomplete, as laser distance-measurement data is being captured.

Patent's centerline 705 may not exactly be aligned with the stomach as shown in FIG. 10G. Instead, rotation may be around rotational axis 702, FIG. 10H.

In lower region 712, rotational axis 702 is a vertical axis that the rotating ring and magnets rotates around, and this vertical axis typically passes through the person's head and abdomen, depending on the person's exact standing position and physique. While rotational axis 702 passes through the stomach, the non-symmetrical shape of the stomach causes rotational axis 702 to pass through only lower region 712 but not through upper region 710, other than a small portion by the esophagus. When control program creates path 720 that the capsule will follow through the stomach, the control program can rotate capsule 10 when it is near rotational axis 702. However, when capsule 10 is far from rotational axis 702, such as in upper region 710, rotation of rotating ring 40 could cause capsule 10 to hit the stomach wall.

The control program performs rotation primarily in lower region 712. The control program uses mostly X and Z motions when generating path 722 in upper region 710. The control program generates path 720 by rotating the capsule when it is near rotational axis 702 in lower region 712, and also uses X and Z motions, being careful to only have movements that fall within the interion of stomach map 704. The control program generates path 722 without fully rotating the capsule in upper region 710, and only uses partial rotations to adjust camera angle, and X and Z motions, being careful to only have movements that fall within the interior of stomach map 704. The control program may combine many paths 722 that each trace a different vertical slice of stomach map 702 in the 3D map. When rotation is needed, the control program can return capsule 10 to rotational axis 702 in lower region 712 for rotation, before returning to upper region 710. Many path and movement variations are possible.

When using lasers to map the stomach wall, path 722 may stay near the center of the stomach. When capturing images using front camera 72 and side camera 82, capsule 10 may be moved closer to the stomach wall for better and more precise imaging. Thus path 722 may differ for laser mapping and visible light imaging.

Figure 11A:
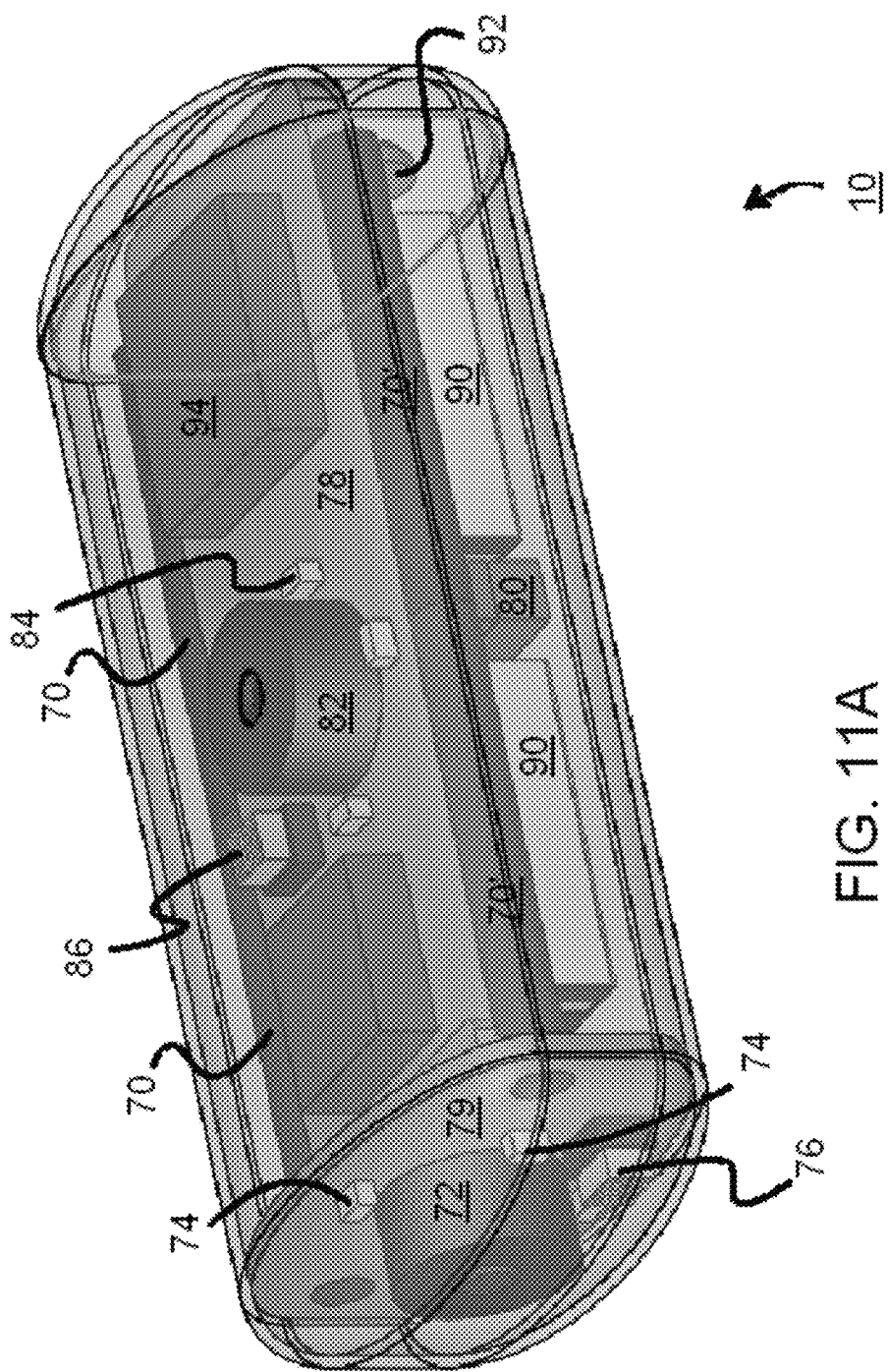

FIGS. 11A-11D show the magnetic endoscopy capsule in more detail. In FIG. 11A, in the top front view, capsule 10 has front camera 72 facing left along with its four LEDs 74 and front laser 76, which can be mounted to front PCB 79 that is mounted orthogonally to PCB 78.

The top of PCB 78 has side camera 82 mounted to it, along with LEDs 84 and side laser 86. Controller 94 is also mounted to PCB 78, along with other components. Battery 90 is placed below PCB 78 and can have more than one module. Flip magnet 80 fits between the two modules of battery 90, below PCB 78. Antenna 92 is mounted to the far end of PCB 78, facing the back in this view.

Rather than have a single primary magnet 70, in this embodiment there are two primary magnets 70, 70', placed on both sides of PCB 78. Having two primary magnets 70, 70', rather than a single magnet, allows for side camera 82 to be placed in the center of PCB 78 and of capsule 10. Having two primary magnets 70. 70' that are parallel to each other allows for better balancing of the external magnetic forces transferred to capsule 10.

In FIG. 11B, in the top bottom view, capsule 10 still has front camera 72 facing left along with its four LEDs 74 and front laser 76 mounted on front PCB 79. The top and bottom of PCB 78 have been reversed in this view compared with the view of FIG. 11A, such as after having been flipped by flip magnet 80. Flip magnet 80 is visible on top between the two modules of battery 90. Antenna 92 is visible at the far end. Primary magnet 70 can be seen but primary magnet 70' is hidden from this view.

FIG. 11C is a front view of capsule 10. Front camera 72 is mounted near the center of front PCB 79 and is surrounded by its four LEDs 74. Front laser 76 is also mounted to front PCB 79. The North (N) ends of primary magnet 70 and of primary magnet 70' protrude through holes in this front PCB 79.

FIG. 11D is a rear view of capsule 10. The South(S) ends of primary magnet 70 and of primary magnet 70' are visible on either side of PCB 78. Controller 94 is mounted to the bottom-facing surface of PCB 78 in this view, while battery 90 and flip magnet 80 are placed on the top-facing surface of PCB 78. Antenna 92 is visible in front of the first module of battery 90, and the middle of flip magnet 80 is hidden from view by this first module of battery 90.

Figure 12:
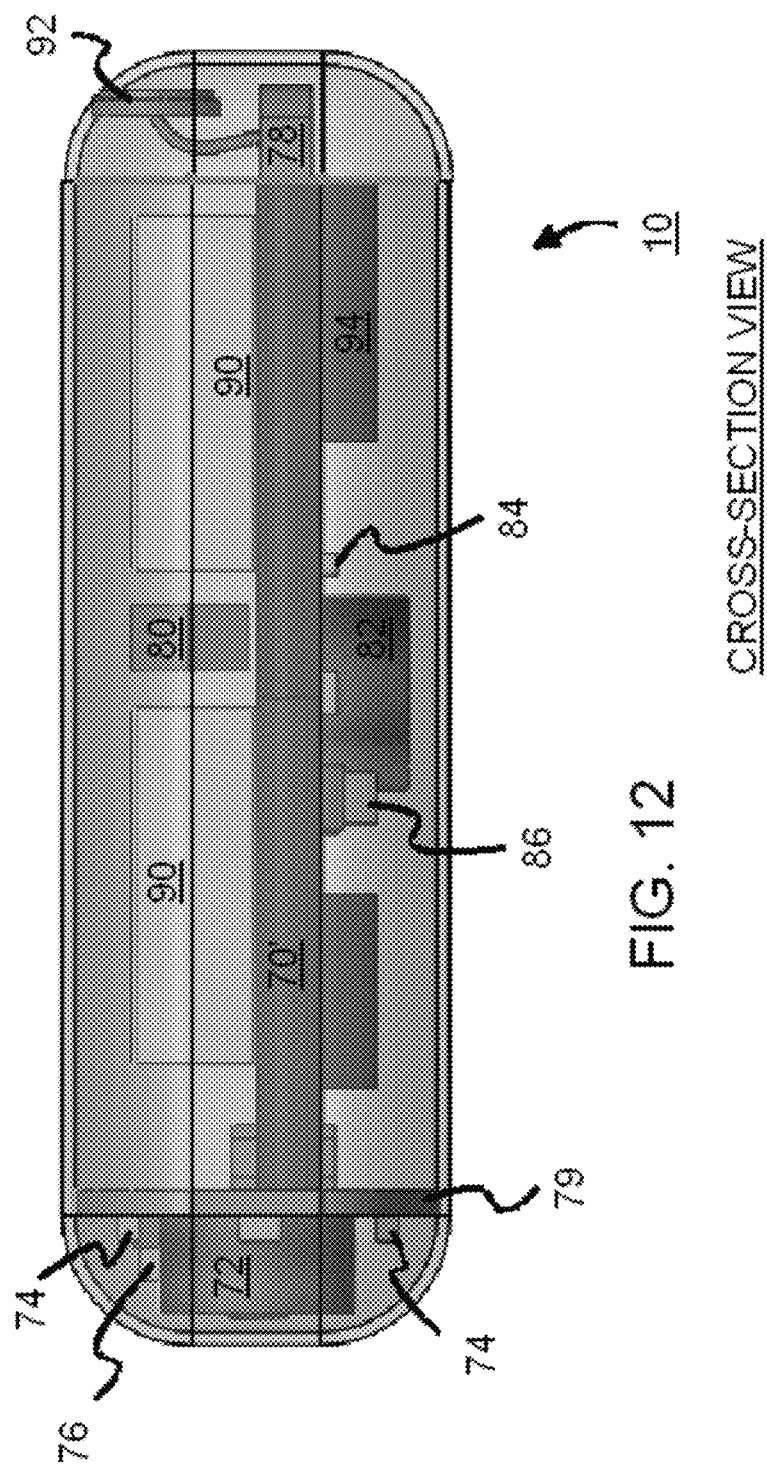
FIG. 12 is a cross-sectional view of the capsule.

FIG. 12 is a cross-sectional view of the capsule. Flip magnet 80 is placed between the two modules of battery 90. PCB 78 runs most of the length of capsule 10, from antenna 92 in the rear to front PCB 79 in the front, with primary magnet 70' hiding most of PCB 78 from view. The N end of primary magnets 70, 70' face left, near front camera 72, while the S ends of primary magnets 70, 70' are near antenna 92. The N end of flip magnet 80 faces up while the S end of flip magnet 80 faces down in this view.

Side camera 82 and its LEDs 84 and side laser 86 are mounted to primary PCB 78. Front PCB 79 is mounted orthogonally and connects to PCB 78. Front camera 71, LEDs 74, and front laser 76 are mounted to front PCB 79.

Figure 4:
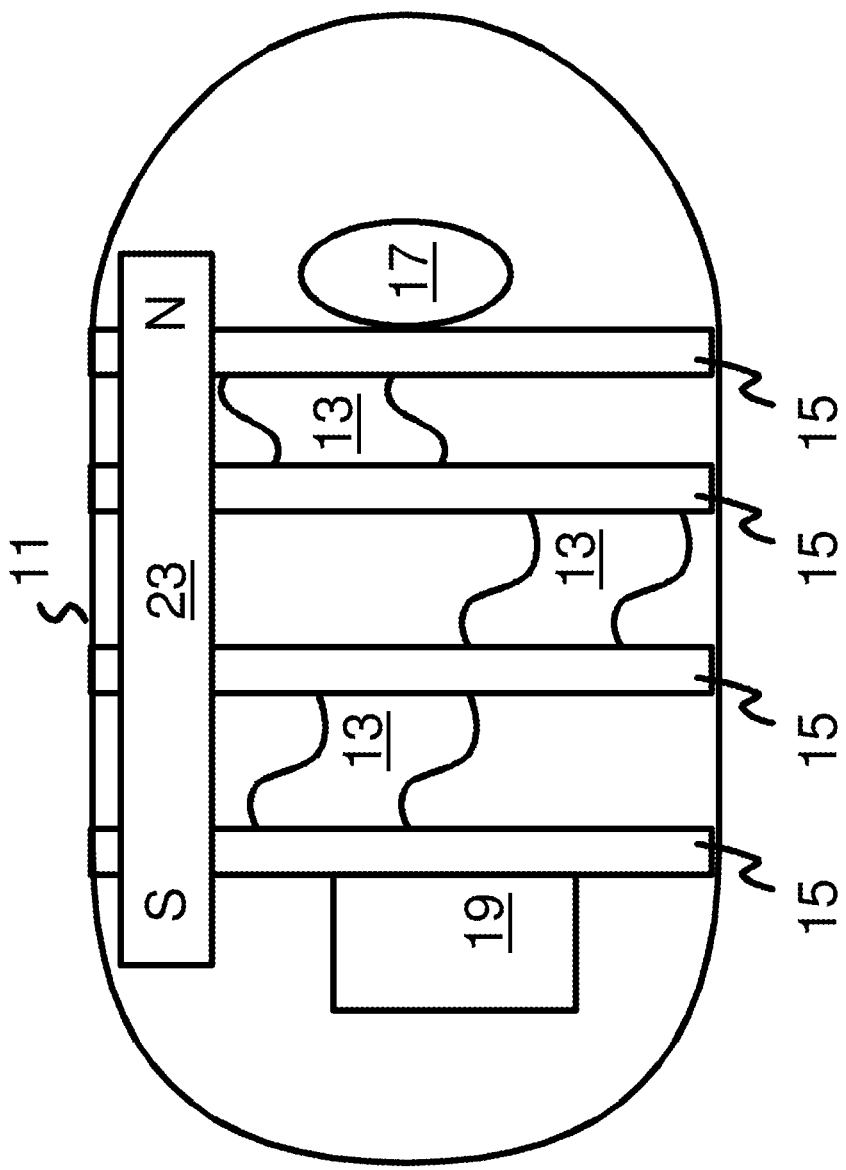
FIG. 4 shows a prior art magnetic endoscopy capsule.

Most components are mounted to primary PCB 78, while the remaining components are mounted to front PCB 79, which is itself mounted to primary PCB 78. Many small circular PCB's and cabling (FIG. 4) are not needed. Cabling is eliminated since front PCB 79 directly attaches to primary PCB 78. Front PCB 79 can be attached to the front edge of primary PCB 78 by direct soldering, a pin connector, a socket, or by some other connector.

Cameras and lasers that are orthogonal to each other are provided by the two orthogonal-mounted PCBs 78, 79. Laser mapping and imaging of the entire stomach wall can be more easily performed when dual sensors are facing in two orthogonal directions. The entire stomach wall can be inspected even with a small pitching range of the capsule.

Alternate Embodiments

Several other embodiments are contemplated by the inventors. For example many combinations and variations of the capsule, control program, hardware, software, firmware, controllers, magnets, poles, clamps, and machine are possible. The lasers could have an array of laser light emitters or generators rather than a single laser emitter. The laser rangefinders could have a dedicated sensor that detects reflected laser light, or could use the camera's image sensor. The camera could be an image sensor such as a Charge-Coupled Device (CCD) or Complimentary Metal-Oxide-Semiconductor (CMOS) sensor, or some hybrid or variation. The image sensor could detect light that includes the laser light's wavelength. The camera may flash the LEDs only when capturing the visible light reflected back to the image sensor, or the LEDs may remain on before and after image capture. The image sensor could also detect Infra Red (IR) light in some embodiments. The LED could emit various wavelengths such as IR, or the IR light may be generated by heat from the stomach wall. There may be multiple LEDs or an LED array.

The image sensor may have a lens of some sort. The casing of capsule 10 could be transparent or could have a transparent section near the image sensors, LEDs and laser emitters. The light sensor may have a high resolution, such as for an image sensor that captures visible light images, or may have little or no resolution, such as a laser-light detector that merely indicates when laser light is received without any image. The light sensor may have several parts, such as an array of R, G, and B detectors for red, green, and blue wavelengths, that form an array for image capture, or a single laser-light detector at the laser-light wavelength that detects the mere presence of reflected laser light.

Base electromagnet 34 can remain off most of the time and be pulsed on for a short period of time when flipping is needed. The amount of time for flipping can be short because of the small rotational inertia of capsule 10, allowing it to roll quickly. Alternately, base electromagnet 34 could remain on or periodically be pulsed on to ensure that capsule 10 remains in the desired orientation.

While orienting capsule 10 to capture images using end camera 72 and side camera 82 has been described, capsule 10 may instead be oriented to use end laser 76 and side laser 86. Laser mapping of the stomach wall may be performed first, before image capture. Since the laser beam can penetrate the stomach fluids better than light from the LEDs, laser mapping of the stomach can be performed with capsule 10 located at just a few central positions, while capsule 10 is moved among many positions closer to the stomach wall for image capture.

The control program can be automated with a computer program selecting what images to capture and mapping the stomach to determine locations to move capsule 10. Thus a skilled medical doctor is not needed to operate the automated magnetic endoscopy machine. Also, since the control program makes decisions about what areas to image, the screening procedure does not have to wait for a human doctor to examine the images and decide on the next movements for further imaging. The speed of the screening procedure can be much faster using the control program than when using a human doctor. This faster screening has the benefit of permitting a smaller battery to be used, with a reduction in the size of capsule 10, compared with human-controlled screening. A larger number of images may be automatically captured possibly providing for better screening.

When the remaining battery life is sufficient near the end of screening, the control program can take additional images of areas where an abnormality is detected in the earlier scan of images. The control program can use Artificial Intelligence (AI) or other tools and may offload images to a remote server for such processing. The remote server can respond with coordinates within the stomach map of areas of interest for the control program to take additional images before the battery dies.

The control program does not require human input. The control program maps the stomach wall and then adjusts the magnets to move capsule 10 through a sequence of locations within the confines of the stomach wall identified by the stomach wall map and captures images of the stomach wall from these various locations. The control program can screen these images for abnormalities, and take additional images when abnormalities are detected. Images with abnormalities can be flagged and sent to a medical doctor or technician for further evaluation, and the person can be referred to a doctor for a traditional endoscopy when such abnormalities are detected by the control program.

The controller inside the magnetic endoscopy capsule may determine the distance to a point on the stomach wall by timing a pulse of light that reflects off the stomach wall, or by analyzing the received light pattern or intensity. The controller may wirelessly transmit the actual distance, or a normalized distance, or the time delay, or some other function of the distance, or the light pattern received by the image sensor, to the external control program. The external control program may modify the reported distance to construct the stomach wall map. The controller may analyze a diffraction pattern that is detected by the image sensor to determine the distance. The diffraction pattern may be analyzed by the controller, or may be sent to an external computer for analysis to determine the distance. The mask that diffracts the laser beam can be a diffraction grating or a small aperture opening. The mask can be part of the laser emitter module or can be a separate mask within the capsule, or may be a window in the capsule that the laser beam passes through.

While two cameras 72, 82 and two lasers 76, 86 have been described for capsule 10, other embodiments may have only one camera or laser, or may have more than two. Capsule 10 may be simplified further or enhanced further. A hard plastic that is impervious to stomach acid may be used for the casing of capsule 10, with clear windows for cameras 72, 82 and LEDs 74, 84, and lasers 76, 86. Capsule 10 may be pill-shaped for easy swallowing.

While laser mapping and imaging of the stomach have been described, capsule 10 eventually passes through the intestines, and imaging of the intestines could also be performed when sufficient battery life is available. The more limited cross-sectional area of the intestines may hinder movement of capsule 10 compared with the larger stomach, and capsule 10 may rapidly move through the intestines regardless of external magnetic fields due to natural intestinal contractions and other processes. Thus the screening procedure may be more difficult to apply to colonoscopies, but is not impossible. Further research with the invention may permit extension to intestinal screening.

While rotating a rotating ring through 360 degrees has been described, this rotation may not require 360 separate measurements. For example, a laser distance measurement or camera image may be obtained only every 10 degrees, for a total of 36 measurements for the entire 360 degree rotation cycle. Fewer measurements may be used for higher latitude regions of the polar map than for equatorial regions that have a larger circumference. The field of view of the camera may affect the number of images per full rotation. A camera with a 45 degree field of view may capture an image for every 36 degrees of rotation, for a total of 10 imaged for a full circle, while a camera with a narrow 15 degree field of vision may require images every 10 degrees, for a total of 36 images for the full rotational circle. The amount of overlap between adjacent images can also be adjusted. Many optimizations are possible.

Various combinations of software, firmware, and hardware may be used to implement various functions and operations. Hardware may provide low-level control of actuators 30, 32, and software may use I/O writes to write commands and values into registers for actuators 30, 32 to control movement, or to magnet current drivers to control current values. Hardware may decode commands and activate low-level control routines, such as to rotate or move components by a specified amount or for a specified time. Many variations and levels of control are possible.

Primary PCB 78 and front PCB 79 may each be a circuit board that is flexible or stiff, and may have various numbers of layers of metal and insulators.

Currents can be positive or negative currents, direct or alternating, and flow in either direction. Many second and third order magnetic and electrical effects may be present and may be significant, but adjusted for through benchmarking.

The magnetic axis of primary magnet 70 could lie exactly along the long or longitudinal axis of capsule 10, or could lie parallel to the long axis of capsule 10. The magnetic axis can be defined as the line passing through both North and South poles. Primary PCB 78 may also lie exactly on the long axis, or may be parallel to the long axis. For example, in FIG. 12 PCB 78 is slightly offset from the centerline of capsule 10, yet is still parallel to the long axis or centerline. When there are two primary magnets 70, 70', they may be offset from the centerline or long axis of capsule 10, yet still parallel to the long axis.

When terms such as perpendicular, orthogonal, and parallel are used, it is understood that there may be variances or offsets that cause slight differences from being exactly perpendicular or parallel. For example, while orthogonal planes are at right angles, the angle may not be exactly 90 degrees, but may be within some tolerance of 90 degrees, such as between 80 and 100 degrees. While the invention operates optimally when primary magnet 70 and flip magnet 80 are 90 degrees from each other, the invention still functions at less efficiencies when the angle between these magnets has a greater offset from 90 degrees. The terms perpendicular and orthogonal are often used interchangeably.

Terms such as up, down, above, under, horizontal, vertical, inside, outside, clockwise, counter-clockwise, etc. are relative and depend on the viewpoint and are not meant to limit the invention to a particular perspective. Devices may be rotated so that vertical is horizontal and horizontal is vertical, so these terms are viewer dependent. While having the patient stand has been described, the patient could be in other positions, such as laying flat, and the term up would refer to the direction from the stomach to the patient's head, and down refer to the direction from the stomach to the patient's feet.

The background of the invention section may contain background information about the problem or environment of the invention rather than describe prior art by others. Thus inclusion of material in the background section is not an admission of prior art by the Applicant.

Any methods or processes described herein are machine-implemented or computer-implemented and are intended to be performed by machine, computer, or other device and are not intended to be performed solely by humans without such machine assistance. Tangible results generated may include reports or other machine-generated displays on display devices such as computer monitors, projection devices, audio-generating devices, and related media devices, and may include hardcopy printouts that are also machine-generated. Computer control of other machines is another tangible result.

Any advantages and benefits described may not apply to all embodiments of the invention. When the word "means" is recited in a claim element, Applicant intends for the claim element to fall under 35 USC Sect. 112, paragraph 6. Often a label of one or more words precedes the word "means". The word or words preceding the word "means" is a label intended to ease referencing of claim elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word "means" are not intended to fall under 35 USC Sect. 112, paragraph 6. Signals are typically electronic signals, but may be optical signals such as can be carried over a fiber optic line.

The foregoing description of the embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

We claim:

1. A dual-beam magnetic endoscopy capsule that is swallowed by a patient, the dual-beam magnetic endoscopy capsule comprising:
   a casing that encloses components inside the dual-beam magnetic endoscopy capsule, the casing having a length that is greater than a width, with a long axis along the length of the casing, the casing being impervious to stomach acid;
   a primary magnet situated inside the casing, the primary magnet having a first magnetic axis that passes through a North and a South pole of the primary magnet, the first magnetic axis being parallel to the long axis;

a second magnet situated inside the casing, the second magnet having a second magnetic axis that passes through a North and a South pole of the second magnet, the second magnetic axis being orthogonal to the long axis;

wherein the primary magnet is longer along the first magnetic axis than the second magnet is long along the second magnetic axis;

a front light sensor situated inside the casing near a front end where the first magnetic axis intersects the casing, the front light sensor for detecting light received that is reflected off a stomach interior at a first point;

a front light source, situated inside the casing near the front end, for generating a front light beam that is reflected off the first point of a stomach interior and reflected back into the front light sensor;

a side light sensor situated inside the casing near a middle of the casing, the side light sensor for detecting light received that is reflected off the stomach interior at a second point;

a side light source, situated inside the casing near the middle of the casing, for generating a side light beam that is reflected off the stomach interior at a second point and back into the side light sensor;

wherein the side light beam is orthogonal to the front light beam;

a controller that controls the front light source to generate the front light beam, and that uses the front light detector to detect the light reflected back from the first point on the stomach interior, the controller determining a first distance from the dual-beam magnetic endoscopy capsule to the first point in response to the front light detector;

wherein the controller also controls the side light source to generate the side light beam, and that uses the side light detector to detect the light reflected back from the second point on the stomach interior, the controller determining a second distance from the dual-beam magnetic endoscopy capsule to the second point in response to the side light detector;

wherein distances to two points on the stomach interior are generated for each location and orientation of the dual-beam magnetic endoscopy capsule within the stomach using two light beams that are orthogonal.

2. The dual-beam magnetic endoscopy capsule of claim 1 wherein the front light beam is a laser light beam, and the front light source comprises a first laser emitter;

wherein the side light beam is a laser light beam, and the side light source comprises a second laser emitter;

wherein the first laser emitter and the second laser emitter are mounted orthogonally within the casing.

3. The dual-beam magnetic endoscopy capsule of claim 2 further comprising:

a primary Printed Circuit Board (PCB), enclosed by the casing, the primary PCB having two surfaces for mounting components, the two surfaces being parallel to the first magnetic axis;

a side camera, mounted on one of the two surfaces of the primary PCB, for capturing images of the stomach interior;

wherein external first electromagnets situated along the first magnetic axis move the dual-beam magnetic endoscopy capsule within the stomach when the external first electromagnets are moved and energized;

wherein an external base electromagnet situated along the second magnetic axis causes the dual-beam magnetic endoscopy capsule to roll around the first magnetic axis when the external base electromagnet is energized and the external first electromagnets are energized and not moving;

wherein the second magnet causes the dual-beam magnetic endoscopy capsule to roll, flipping an orientation of the side light sensor and the side light source, when acted upon by the external base electromagnet, wherein the side light beam reflects off a third point on the stomach interior after flipping by the second magnet;

wherein distances to three points on the stomach interior are generated for each location of the dual-beam magnetic endoscopy capsule within the stomach using two light beams that are orthogonal and rolling the dual-beam magnetic endoscopy capsule.

4. A capsule for swallowing to inspect a stomach comprising:

a casing that encloses components inside the capsule, the casing having a length that is greater than a width, with a long axis along the length of the casing, the casing being resistant to stomach acid;

a primary magnet situated inside the casing, the primary magnet having a first magnetic axis that passes through a North and through a South pole of the primary magnet, the first magnetic axis being parallel to the long axis;

a second magnet situated inside the casing, the second magnet having a second magnetic axis that passes through a North and a South pole of the second magnet, the second magnetic axis being orthogonal to the long axis;

wherein the primary magnet is longer along the first magnetic axis than the second magnet is long along the second magnetic axis;

a front light detector situated inside the casing near a front end where the first magnetic axis intersects the casing, the front light detector for detecting light received that is reflected off a stomach interior at a first point;

a front laser emitter, situated inside the casing near the front end, for generating a front laser beam that is reflected off the first point of a stomach interior and reflected back into the front light detector;

a side light detector situated inside the casing near a middle of the casing, the side light detector for detecting light received that is reflected off the stomach interior at a second point;

a side laser emitter, situated inside the casing near the middle of the casing, for generating a side laser beam that is reflected off the stomach interior at a second point and back into the side light detector;

wherein the side laser beam is orthogonal to the front laser beam;

a controller that controls the front laser emitter to generate the front laser beam, and that uses the front light detector to detect the light reflected back from the first point on the stomach interior, the controller determining a first distance from the capsule to the first point in response to the front light detector;

wherein the controller also controls the side laser emitter to generate the side laser beam, and that uses the side light detector to detect the light reflected back from the second point on the stomach interior, the controller determining a second distance from the capsule to the second point in response to the side light detector;

wherein distances to two points on the stomach interior are generated for each location and orientation of the capsule within the stomach using two laser beams that are orthogonal;

wherein the front laser emitter and the side laser emitter are mounted orthogonally within the casing;

a Light-Emitting Diode (LED) for illuminating the stomach interior; and an image sensor for capturing an image of light from the LED that is reflected back to the image sensor.

5. The capsule of claim 4 further comprising:

a primary Printed Circuit Board (PCB), enclosed by the casing, the primary PCB having two surfaces for mounting components, the two surfaces being parallel to the first magnetic axis;

wherein the controller, the side laser emitter, and the side light detector are mounted to the primary PCB.

* * * * *